United States Patent
Vogler et al.

(10) Patent No.: US 9,649,023 B2
(45) Date of Patent: May 16, 2017

(54) SYSTEM AND METHOD FOR DETERMINING BIOMETRIC PROPERTIES OF AN EYE

(71) Applicant: Novartis AG, Basel (CH)

(72) Inventors: Klaus Vogler, Eckental (DE); Christof Donitzky, Eckental (DE)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 14/778,051

(22) PCT Filed: Dec. 5, 2013

(86) PCT No.: PCT/EP2013/075601
§ 371 (c)(1),
(2) Date: Sep. 17, 2015

(87) PCT Pub. No.: WO2015/082001
PCT Pub. Date: Jun. 11, 2015

(65) Prior Publication Data
US 2016/0278631 A1    Sep. 29, 2016

(51) Int. Cl.
*A61B 3/10* (2006.01)
*A61B 3/00* (2006.01)
(Continued)

(52) U.S. Cl.
CPC .......... *A61B 3/1005* (2013.01); *A61B 3/0025* (2013.01); *A61B 3/102* (2013.01);
(Continued)

(58) Field of Classification Search
CPC ......... A61B 3/102; A61B 3/14; A61B 3/1005; A61B 3/107
(Continued)

(56) References Cited

U.S. PATENT DOCUMENTS

2010/0290007 A1*  11/2010  Van de Velde ........ A61B 3/102
                                                                351/221

FOREIGN PATENT DOCUMENTS

EP         2404545 A2    1/2012
WO     2013/134554 A1   9/2013

OTHER PUBLICATIONS

Grulkowski et al: "Retinal, anterior segment and full eye imaging using ultrahigh speed swept source OCT with vertical-cavity surface emitting lasers", Biomedical Optics Express, vol. 3, No. 11, Nov. 1, 2012 (Nov. 1, 2012), pp. 2733-2751, XP055133476, ISSN: 2156-7085, DOI: 10.1364/BOE.3.002733 abstract; figures 2,11,; tables 1,2 p. 2739, paragraph 3-p. 2742, paragraph 3.
(Continued)

*Primary Examiner* — Hung Dang

(57) ABSTRACT

In certain embodiments, determining biometric properties of an eye includes emitting a measuring light beam. The measuring light beam is guided towards the eye for a plurality of scans. For each scan, the measuring light beam enters the cornea in a first lateral region and reaches the retina of the eye in a second lateral region along a corresponding beam path. The beam paths are different from each other. The measuring light beam back-reflected from the eye for each scan is interferometrically analyzed to provide corresponding OCT data. At least one of the following is determined according to the OCT data: at least one distance from a surface of the retina to a surface of the cornea or to a surface of the lens of the eye.

12 Claims, 3 Drawing Sheets

Figure 1:
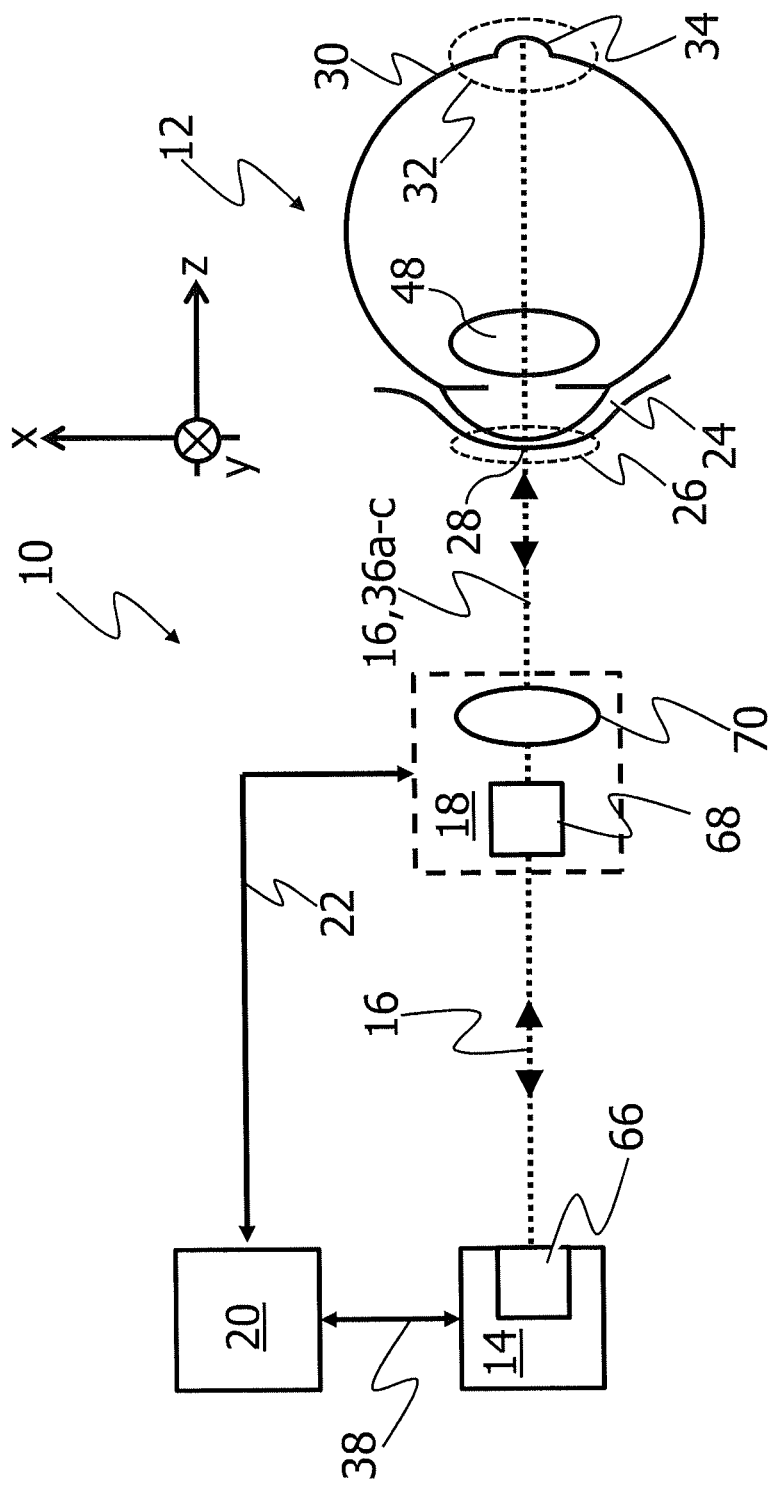

(51) Int. Cl.
*A61B 3/12* (2006.01)
*G02B 26/08* (2006.01)
*H01S 5/183* (2006.01)

(52) U.S. Cl.
CPC ........ *A61B 3/1225* (2013.01); *G02B 26/0833* (2013.01); *H01S 5/183* (2013.01)

(58) Field of Classification Search
USPC .......................... 351/212, 211, 246, 205, 221
See application file for complete search history.

(56) References Cited

OTHER PUBLICATIONS

Zhong et al: "Axial Biometry of the Entire Eye Using Ultra-Long Scan Depth Optical Coherence Tomography", American Journal of Ophthalmology, vol. 157, No. 2; Oct. 7, 2013 (Oct. 7, 2013), pp. 412-420.e2, XP055133041, ISSN: 0002-9394, DOI: 10.1016jj.ajo. 2013.09.033.

* cited by examiner

SYSTEM AND METHOD FOR DETERMINING BIOMETRIC PROPERTIES OF AN EYE

CROSS REFERENCE TO RELATED APPLICATIONS

This application is a section 371 national stage phase of International Application No. PCT/EP2013/075601, filed 5 Dec. 2013, titled "SYSTEM AND METHOD FOR DETERMINING BIOMETRIC PROPERTIES OF AN EYE," which is hereby incorporated by reference in its entirety.

TECHNICAL FIELD

The present disclosure relates to a system, for example, for determining biometric properties of an eye and a method, for example, for determining biometric properties of an eye.

BACKGROUND

Various different surgical eye treatments exist, such as photorefractive keratectomy (short: PRK) and laser assisted in-situ keratomileusis (short: LASIK) for improving visual acuity of the eye by correction of myopia, hypermetropia, astigmatism or the like, or cataract surgery for implanting an intraocular lens.

For the individual preparing and planning of such surgical eye treatments, determination of biometric properties of the eye is required by identifying the geometrical characteristics of the eye to be treated.

Existing systems for determining biometric properties of an eye employ a measuring light beam for providing data, which represent distances between surfaces on or in the eye, such as surfaces of the cornea, the lens and the retina of the eye. So far, the data provided by such existing systems merely represent the distances along a single beam path of the measuring light beam, i.e. existing systems determine biometric properties of the eye on basis of only a single scan.

However, because of the eye's geometry, the measured distances between the surfaces on or in the eye depend on the specific optical beam path, along which the measuring light beam propagates through the eye. These beam path dependent distances result in uncertainties of the biometric properties determined by the existing systems. Furthermore, by the existing systems for determining biometric properties of an eye it cannot be extracted, along which specific beam path the measuring light beam propagated during the single scan.

Therefore, it is desirable reduce or even avoid uncertainties in determined biometric properties of an eye.

SUMMARY

In light of the above, there is a need to provide a system and a method, which allow a precise determining of biometric properties of an eye.

In the present disclosure, a system for determining biometric properties of an eye and a method for determining biometric properties of an eye are provided.

A system for determining biometric properties of an eye, for example, a human eye, an animal eye or an artificial eye comprises an OCT device, which is configured to emit a measuring light beam. The system also comprises a beam guiding device, which is configured to guide the measuring light beam. Further, the system comprises a control and analysis device, which is configured to control the beam guiding device to guide the measuring light beam towards the eye for a plurality of scans such that for each scan the measuring light beam enters the cornea in a first lateral region and reaches the retina of the eye in a second lateral region including the fovea of the retina along a corresponding beam path, wherein the beam paths are different among each other. The OCT device is further configured to interferometrically analyze the measuring light beam back-reflected (or back-scattered or back-deflected) from the eye for each scan to provide corresponding OCT data. The control and analysis device is further configured to determine on basis of the OCT data for each scan of the plurality of scans at least one distance from a surface of the retina to a surface of the cornea and/or to a surface of the lens, for example, a human lens, an animal lens or an artificial lens, like intraocular lens (short: IOL) of the eye.

As an advantage of this system, for determining biometric properties of the eye, not only a single scan is performed, which provides OCT data representing distances only along a single beam path of the measuring light beam. Rather, for determining the biometric properties of the eye the present system performs a plurality of scans, wherein for each scan the measuring light beam may propagate along a different, i.e. separate/unique beam path between the first lateral region, which may include, for example, the apex and/or the vertex of the cornea, and the second lateral region including the fovea of the retina such that the plurality of determined distances represents not only an axial mapping, but also an at least partially lateral mapping of the distances between the eye components, such as the cornea, the lens and the retina, and of the thicknesses of these eye components. As a result, the system not only allows an axial determining of biometric properties of the eye, but also an at least partially lateral determining of the biometric properties of the eye. Further, the system allows, for example, an averaging of the determined distances on basis of the plurality of scans. Thus, uncertainties, as such arising from a determining of the biometric properties of the eye by performing only a single scan, can be reduced or even be avoided. Hence, the system allows precise determining of biometric properties of the eye.

The surface of the cornea may be the anterior surface of the cornea or the posterior surface of the cornea. Additionally or alternatively, the surface of the cornea may be the corneal epithelium, Bowman's layer (also called anterior limiting membrane/layer), the corneal stroma (also called substantia propria), Dua's layer, Descemet's membrane (also called posterior limiting membrane) and combination of Dua's layer and Descemet's membrane or the corneal endothelium or a surface of one of these cornea components. The surface of the lens of the eye may be the anterior surface of the lens or the posterior surface of the lens.

The control and analysis device may be configured to determine on basis of the OCT data, from the plurality of scans, the surface of the retina, the surface of the lens and/or the surface of the cornea, for example, by feature recognition.

The control and analysis device may be configured to select on basis of the OCT data from the plurality of scans that scan, for which the distance from the surface of the retina to the surface of the cornea or to the surface of the lens is maximum. Further, the control and analysis device may be configured to output the OCT data of this selected scan.

These features have the following advantages:

The visual axis of the eye may be defined as a beam path of a measuring light beam, which enters the eye via the cornea and passes to the fovea of the retina, for example, to the center or the crater bottom of the fovea of the retina. Since the fovea is responsible for sharp central vision (also called foveal vision), which is necessary for any activity, where visual detail is of primary importance, a determining of biometric properties of the eye along the visual axis of the eye may be considered to be most valuable or even mandatory for individual preparing and planning surgical eye treatments.

The geometry of the fovea within the retina is comparable to a small crater, which has a diameter of around 400 µm to around 500 µm and a depth of around 100 µm and whose crater bottom extends away from a center of the eye. As a consequence of the fovea's geometry, a distance from the surface of the fovea to a predetermined surface of, for example, the cornea or the eye's lens is larger compared to a distance from the surface of the retina neighbored to the fovea to the predetermined surface.

In light of the above, by selecting the scan, for which the distance from the surface of the retina to the surface of the cornea or to the surface of the lens is maximum, it is also selected the beam path, along which the measuring light beam runs also along or at least close to the visual axis of the eye. In other words: The selected scan may be associated with a scan, which represents best a determining of biometric properties of the eye along the visual axis of the eye. Therefore, the output OCT data of the selected scan represents best the central thicknesses of the cornea and/or of the lens as well as the distances from the surface of the retina to the surface of the cornea or to the surface of the lens along the visual axis of the eye. Thus, the output OCT data of the selected scan represents the most valuable data for an individual preparing and planning of a surgical treatment on the eye. This allows preparing, planning and performing of precise surgical results.

The control and analysis device may be configured to calculate on basis of the OCT data from the plurality of scans appropriate parameters of an IOL (such as, for example, the refraction power and the asphericity of the IOL) and/or to calculate on basis of the OCT data from the plurality of scans an appropriate position and orientation of the IOL within the lens. As a result, for preparing, planning and performing a surgical eye treatment to implement an IOL, it is helpful to know the correct eye distances, for example, within the lens, because depending on these correct eye distances, on the one hand, the IOL can be correctly selected with appropriate IOL parameters (such as, for example, the refraction power and the asphericity of the IOL) and, on the other hand, the IOL can be correctly placed in the lens.

The control and analysis device may be configured to determine on basis of the OCT data of the selected scan a position of the intersection point of the cornea and/or the intersection point of the lens and/or a position of a center or a crater bottom of the fovea. This allows an identification of the visual axis of the eye. For example, the control and analysis device may be configured to determine the visual axis of the eye by associating the visual axis of the eye with a straight line through the thus determined position of the intersection point of the cornea and/or through the thus determined position of the center and/or the crater bottom of the fovea.

The intersection point of the cornea may be understood as the point on or in the cornea or the point on or in the anterior or posterior surface of the cornea, where the measuring light beam intersects or penetrates or impinges the cornea, for example, by the visual axis. The intersection point of the lens may be understood as the point on or in the lens or the point on or in the anterior or posterior surface of the lens, where the measuring light beam intersects or penetrates or impinges the lens, for example, by the visual axis.

Additionally or alternatively, the control and analysis device may be configured to determine on basis of the OCT data of the plurality of scans a position of the center and/or the crater bottom of the fovea. Additionally or alternatively, the control and analysis device may be configured to determine on basis of the OCT data of the plurality of scans a position of the intersection point of the cornea or a position of the apex and/or the vertex of the cornea. Additionally or alternatively, the control and analysis device may be configured to determine on basis of the OCT data of the plurality of scans for each scan a position of the intersection point of the cornea. This allows a precise identification of the visual axis of the eye. For example, the control and analysis device may be configured to determine the visual axis of the eye by associating the visual axis of the eye with a straight line through the position of the apex or vertex of the cornea and/or the position of the intersection point of the cornea and through the position of the center and/or the crater bottom of the fovea. As a result, further information for precising the biometric properties of the eye may be determined.

The control and analysis device may be configured to determine on basis of the OCT data of the plurality of scans via ray-tracing, whether the measuring light beam of a specific scan runs through the intersection point of the cornea or the apex and/or the vertex of the cornea, where the measuring light beam of the specific scan impinges on the retina, and/or whether the measuring light beam of the specific scan impacts the fovea of the retina. This allows extracting even more information from the obtained OCT data and a more precisely determining of the biometric properties of the eye.

The control and analysis device may be configured to control the beam guiding device such that the first lateral region is a circular region having a diameter of approximately equal to or less than 1 mm and/or such that the second lateral region including the fovea of the retina is a circular region having a diameter of approximately equal to or less than 1 mm. For example, the control and analysis device may be configured to control the beam guiding device such that the first lateral region include or cover the intersection point of the cornea or may include or cover the apex and/or the vertex of the cornea. The center of the first lateral region may be associated with the apex and/or vertex of the cornea. The center of the second lateral region including the fovea of the retina may be associated with the center or the crater bottom of the retina. This has the advantage that the plurality of scans covers a respective lateral region around the apex and/or vertex of the cornea and/or around the center or the crater bottom of fovea, which is dimensioned such that the visual axis of the eye can reliably be determined.

The OCT device may be understood as optical coherence tomography device. The OCT device may be a Fourier-domain (short: FD) optical coherence tomography device. For example, the OCT device may be a spectral domain (short: SD) optical coherence tomography device for emitting a spectral broadband measuring light beam having an adjustable spectral bandwidth $\Delta\lambda$. The OCT device may be a swept source (short: SS) optical coherence tomography (also called (FD-)SS-OCT) device for emitting a spectral narrowband measuring light beam, which has an adjustable instantaneous spectral bandwidth $\delta\lambda$ and which is swept over an adjustable spectral bandwidth $\Delta\lambda$. The OCT device may be a time-domain (short: TD) optical coherence tomography device which translates longitudinally in time the path length of the reference arm. The term OCT may also be understood as meaning an optical low coherence reflectometry measurement (short: OLCR) device. The OCT device may be configured such that the spectral bandwidth Δλ is approximately equal to or more than 100 nm. Such an OCT device has the advantage that the axial resolution δz of the OCT data can be adjusted via $\delta z=(2 \cdot \ln 2 \cdot \lambda^2)/(n \cdot Pi \cdot \Delta\lambda)$, where n is the refracting index and λ is the central wavelength of the spectrum. The OCT device may be configured such that the axial resolution δz is approximately equal to or less than 10 μm. An SS-OCT device has the further advantage that the scan depth $z_{max}$, i.e. the effective imaging depth, can be adjusted via $z_{max}=(\lambda^2)/(4 \cdot n \cdot \delta\lambda)$. The OCT device may be configured such that the scan depth $z_{max}$ is approximately equal to or more than 40 mm. This allows determining all relevant distances in an eye.

The OCT device may comprises a micro electro mechanical system with vertical cavity surface emitting laser (short: MEMS-VCSEL) device for emitting the measuring light beam. The MEMS-VCSEL device may be configured as an SS-OCT device. As an MEMS-VCSEL device has a small and compact design, the weight and the volume of the whole system can be reduced. Furthermore, a MEMS-VCSEL device has the advantage of providing a high sweep rate for performing the scans. The sweep rate may be around 100 kHz to around 1 MHz. This allows a rapid acquisition the OCT data and thus a reduction of the biometric properties determination time.

A method for determining biometric properties of an eye or a part of the eye comprises the steps:

emitting a measuring light beam,
guiding the measuring light beam towards the eye for a plurality of scans such that for each scan the measuring light beam enters the cornea in a first lateral region and reaches the retina of the eye in a second lateral region including the fovea of the retina along a corresponding beam path, the beam paths being different among each other,
interferometrically analyzing the measuring light beam back-reflected (or back-scattered or back-deflected) from the eye for each scan to provide corresponding OCT data, and
determining on basis of the OCT data for each scan of the plurality of scans at least one distance from a surface of the retina to a surface of the cornea and/or to a surface of the lens of the eye.

To the extent that a method or individual steps of a method is/are described in this description, the method or individual steps of the method can be executed by an appropriately configured system and/or an individual device of the system. Analogous remarks apply to the elucidation of the operation mode of a system and/or individual devices of the system that execute(s) method steps. To this extent, system (i.e. apparatus) features and method features of this description are equivalent.

The term axial may be understood as meaning along the propagation direction of the measuring light beam and/or along the visual axis of the eye. The term lateral may be understood as meaning perpendicular to the propagation direction of the measuring light beam direction and/or along the visual axis of the eye.

Since an above described system allows determining biometric properties of an eye, such a system may also be called a biometer. Similar, since an above described method allows determining biometric properties of an eye, such a method may also be called a biometric method or a method for operating a biometer.

Figure 2:
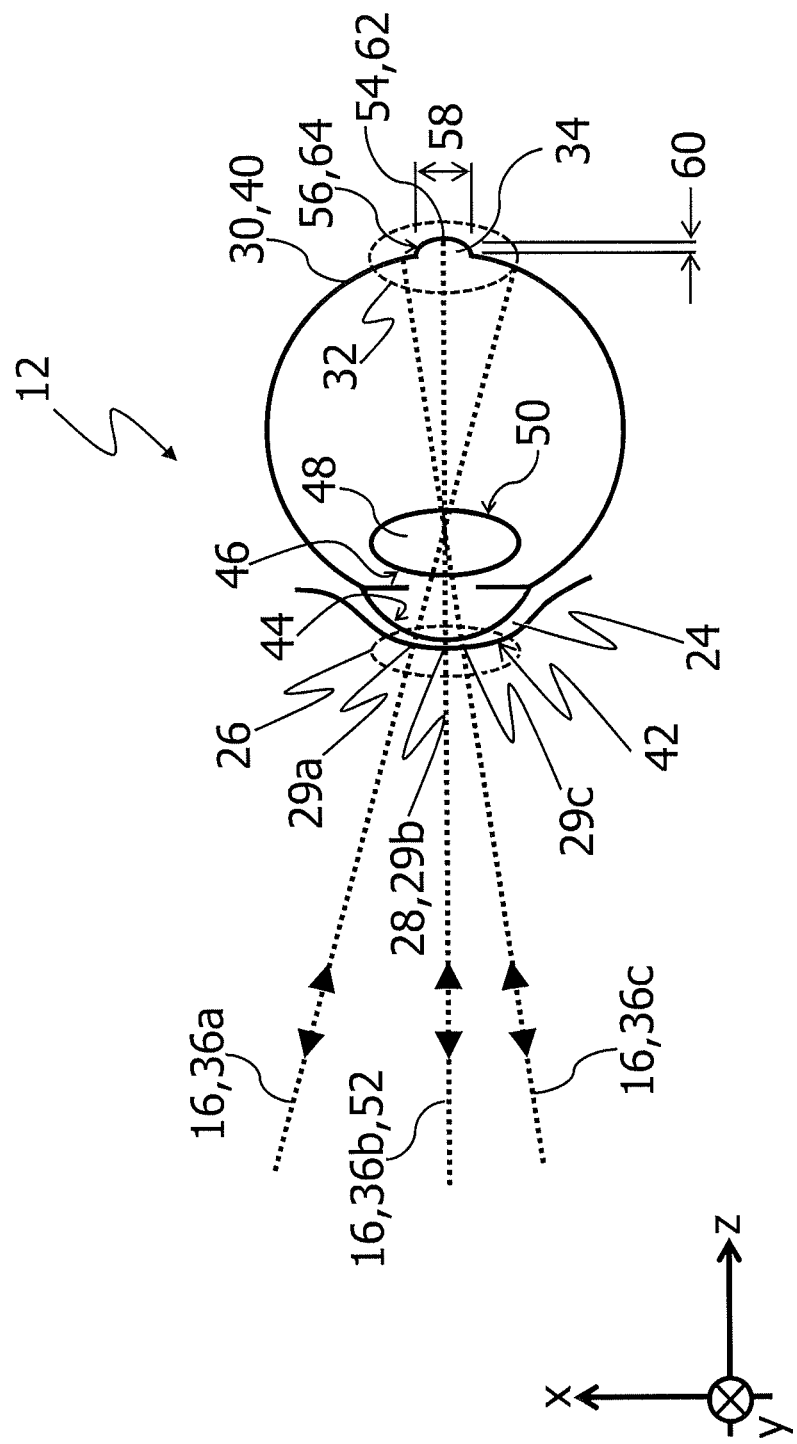
Figure 3:
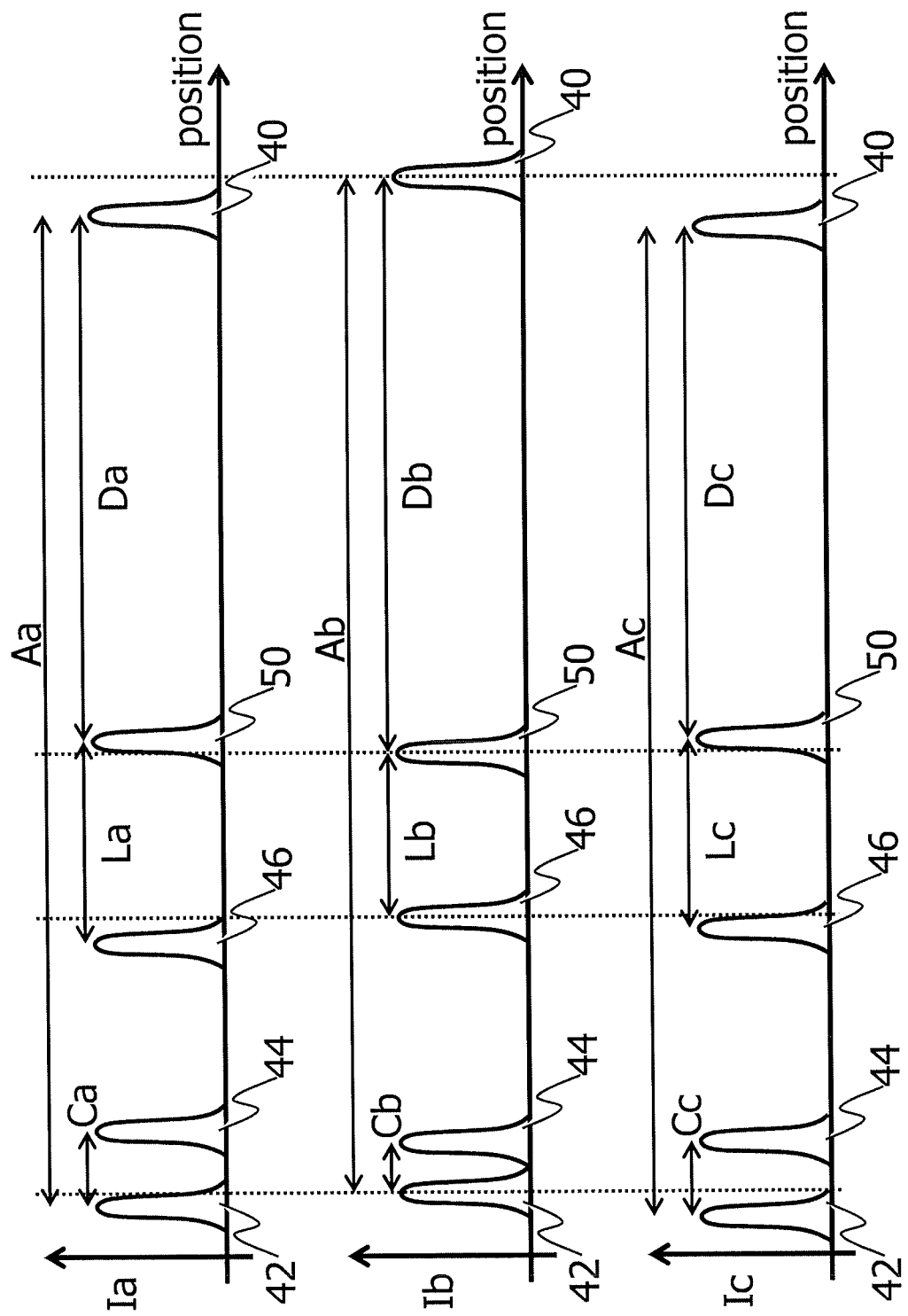

Further features, advantages and technical effects of the disclosure will become apparent from the following description of exemplary embodiments with reference to the accompanying drawings, in which:

FIG. 1 schematically illustrates a system for determining biometric properties of an eye (not drawn to scale), FIG. 2 schematically illustrates a method executed by the system of FIG. 1 (not drawn to scale), and FIG. 3 schematically illustrates OCT data provided and analyzed by the system of FIG. 1 (not drawn to scale).

FIG. 1 shows a system 10 for determining biometric properties of an eye 12. The eye 12 to be examined is, for example, a human eye, an animal eye or an artificial eye.

The system 10 comprises an OCT device 14, which is configured to emit a measuring light beam 16.

The system 10 further comprises a beam guiding device 18, which is configured to guide the measuring light beam 16. A control and analysis device 20 of the system 10 is exemplary connected to the beam guiding device 18 via line 22 and configured to control the beam guiding device 18 to guide the measuring light beam 16 towards the eye 12 for a plurality of scans a, b, c such that for each scan a, b, c the measuring light beam 16 enters the cornea 24 of the eye 12 at respective intersection point 29a, 29b, 29c in a first lateral region 26 and reaches the retina 30 of the eye 12 in a second lateral region 32 including the fovea 34 of the retina 30 along a corresponding beam path 36a, 36b, 36c (see FIGS. 1 and 2). The beam paths 36a-c are different among each other (see FIG. 2).

The OCT device 14 is further configured to interferometrically analyze the measuring light beam 16 back-reflected (or back-scattered or back-deflected) from the eye 12 for each scan a-c to provide OCT data Ia, Ib, Ic (see FIG. 3). The OCT data Ia-c is a position dependent intensity signal representing the eye profile along the corresponding beam path 36a-c. For each specific scan a-c, the intersection point 29a-c of the cornea 24 is understood as the point on or in the cornea 24, where the measuring light beam 16 during the specific scan a-c intersects or penetrates or impinges the cornea 24.

The control and analysis device 20 is exemplary connected to the OCT device 14 via line 38 for receiving the OCT data Ia-c and configured to determine on basis of the OCT data Ia-c for each scan a-c of the plurality of scans by feature recognition, for example, a distance Aa, Ab, Ac from a surface 40 of the retina 30 to an anterior surface 42 or a posterior surface 44 of the cornea 24 as well as a distance Da, Db, Dc from the surface 40 of the retina 30 to an anterior surface 46 of the lens 48 of the eye 12 or to a posterior surface 50 of the lens 48 of the eye 12 (see FIGS. 2 and 3). The control and analysis device 20 is also configured to determine on basis of the OCT data Ia-c for each scan a-c of the plurality of scans a distance Ca, Cb, Cc from the anterior surface 42 of the cornea 24 to the posterior surface 44 of the cornea 24 as well as a distance La, Lb, Lc from the anterior surface 46 of the lens 48 to the posterior surface 50 of the lens 48 (see FIG. 3).

An advantage of system 10, for determining biometric properties of the eye 12 is, that not only a single scan is performed, which provides OCT data I representing distances only along a single beam path of the measuring light beam 16. Rather, for determining the biometric properties of the eye 12, system 10 performs a plurality of scans a-c, wherein for each scan a-c the measuring light beam 16 propagates along a different beam path 36a-c between the first lateral region 26 and the second lateral region 32 including the fovea 34 of the retina 30 such that the plurality of determined distances Aa-c, Da-c, Ca-c, La-c represents not only an axial mapping (corresponding substantially to the z-axis of the coordinate system shown in FIGS. 1 and 2), but also an at least partially lateral mapping (corresponding substantially to the x- and y-axis of the coordinate system shown in FIGS. 1 and 2) of the distances Aa-c, Da-c between the cornea 24, the lens 48 and the retina 30, as well as of the thicknesses Ca-c, La-c of the cornea 24 and the lens 48. As a result, system 10 not only allows an axial determining of biometric properties of the eye 12, but also an at least partially lateral determining of the biometric properties of the eye 12. Further, system 10 allows an averaging of the determined distances Aa-c, Da-c, Ca-c, La-c on basis of the various different scans a-c. Thus, uncertainties, as such arising from a determining of the biometric properties of the eye 12 by only performing a single scan, can be avoided. Hence, system 10 allows a precise determining of biometric properties of the eye 12.

The control and analysis device 20 is also configured to select on basis of the OCT data Ia-c from the plurality of scans a-c that scan b, for which the distance Db from the surface 40 of the retina 30 to the posterior surface 50 of the lens 48 is maximum (compare, for example, the dotted lines in FIG. 3). Then, the control and analysis device 20 outputs the OCT data Ib of the selected scan b.

These features have the following advantages: The visual axis 52 of the eye 12 is exemplarily defined as a beam path of a measuring light beam 16, which enters the eye 12 via the cornea 24 and passes to the center 54 of the fovea 34 of the retina 30. Since the fovea 34 is responsible for sharp central vision (also called foveal vision), which is necessary for any activity, where visual detail is of primary importance, a determining of biometric properties of the eye 12 along the visual axis 52 of the eye 12 is considered to be most valuable or even mandatory, for example, for individual preparing and planning refractive correcting surgical treatments on the eye 12. The geometry of the fovea 34 within the retina 30 is comparable to a small crater 56, which has a diameter 58 of around 400 μm to around 500 μm and a depth 60 of around 100 μm and whose crater bottom 62 extends away from a center (in the vicinity of 48) of the eye 12. As a consequence of the fovea's geometry, the distances Ab, Db from a surface 64 of the fovea 30 to the anterior surface 42 of the cornea 24 and the posterior surface 50 of the lens 48 is larger compared to a distance Aa, Ac, Da, Dc from the surface 40 of the retina 30 neighbored to the surface 64 of the fovea 34 to the anterior surface 42 of the cornea 24 and the posterior surface 50 of the lens 48, respectively. Therefore, by selecting the scan b, for which the distance Ab, Db from the surface 40, 64 of the retina 30 to the surface 42 of the cornea 24 and to the surface 50 of the lens 48, respectively, is maximum, it is also selected the beam path 36b, along which the measuring light beam 16 of the selected scan b runs along or even close to the visual axis 52 of the eye 12. In other words: The selected scan b is associated with a scan, which represents best a determining of biometric properties of the eye 12 along the visual axis 52 of the eye 12. Therefore, the output OCT data Ib of the selected scan b represents best the central thickness Cb of the cornea 24 and the central thickness Lb of the lens 48 as well as the distance Db from the surface 40, 64 of the retina 30 to the anterior surface 42 of the cornea 24 and to the posterior surface 50 of the lens 48 along the visual axis 52 of the eye 12. Thus, the output OCT data Ib of the selected scan b represents the most valuable data for an individual preparing and planning of, for example, refractive correcting surgical treatments on the eye 12. This allows precise refractive correcting results.

The control and analysis device 20 is further configured to determine on basis of the OCT data Ib of the selected scan b, a position of the intersection point 29b of the cornea 24 and a position of a center or a crater bottom 62 of the fovea 34 and to determine the visual axis 52 of the eye 12 by associating the visual axis 52 of the eye 12 with a straight line through the position of the intersection point 29b of the cornea 24 and through the position of the center and/or the crater bottom 62 of the fovea 34.

The control and analysis device 20 is further configured to determine on basis of the OCT data Ia-c of the plurality of scans a-c a position of the crater bottom 62 of the fovea 34 and may a position of the apex and/or vertex 28 of the cornea 24. As a result, further information for precising the biometric properties of the eye 12 can be determined.

The control and analysis device 20 is also configured to determine on basis of the OCT data Ia-c of the plurality of scans a-c via ray-tracing, whether the measuring light beam 16 of a specific scan a-c runs through an intersection point 29b of the cornea 24 or through the apex and/or vertex 28 of the cornea 24, where the measuring light beam 16 of the specific scan a-c intersects or penetrates the cornea 24, where the measuring light beam 16 of the specific scan a-c impinges on the retina 30 and whether the measuring light beam 16 of the specific scan a-c impacts the fovea 34. This allows extracting even more information from the obtained OCT data Ia-c and a more precisely determining of the biometric properties of the eye 12.

In the present example, the control and analysis device 20 may also be configured to control the beam guiding device 18 such that the first lateral region 26 includes or covers the intersection point 29b of the cornea 24 or further includes or covers the apex and/or the vertex 28 of the cornea 24 and/or such that the first lateral region (26) is a circular region of the first lateral region (26) having a diameter of approximately equal to or less than 1 mm and such that the second lateral region 32 including the fovea 34 of the retina 30 is a circular region having a diameter of approximately equal to or less than 1 mm. This has the advantage that the plurality of scans a-c covers a respective lateral region around the intersection point 29b of the cornea 24 and/or around the apex and/or vertex 28 of the cornea 24 and around the crater bottom 62 of fovea 34, which is dimensioned such that the visual axis 52 of the eye 12 can reliably be determined.

The OCT device 14 may be understood as optical coherence tomography device. In the present example, the OCT device 14 is a Fourier-domain (short: FD) OCT device, for example, a swept source (short: SS) OCT (also called (FD-)SS-OCT) device for emitting a spectral narrowband measuring light beam 16, which has an adjustable instantaneous spectral bandwidth δλ and which is swept over an adjustable spectral bandwidth Δλ. The OCT device may be a time-domain (short: TD) OCT device, which translates longitudinally in time the path length of the reference arm. The term OCT may be also understood as meaning an optical low coherence reflectometry measurement (short: OLCR) device. To this end, the OCT device 14 comprises a micro electro mechanical system with vertical cavity surface emitting laser (short: MEMS-VCSEL) device 66 for emitting the measuring light beam 16. The OCT device 14 is configured such that the axial resolution δz is approximately equal to or less than 10 μm and such that the spectral bandwidth Δλ is approximately equal to or more than 100 nm. Such an OCT device 14 has the advantage that the axial resolution $\delta z$ of the OCT data Ia-c can be adjusted via $\delta z=(2\cdot\ln 2\lambda^2)/(n\cdot Pi\cdot\Delta\lambda)$, where n is the refracting index and $\lambda$ is the central wavelength of the spectrum. As being an SS-OCT device, the OCT device 14 has the further advantage that the scan depth $z_{max}$, i.e. the effective imaging depth, can be adjusted via $z_{max}=(\lambda^2)/(4\cdot n\cdot\delta\lambda)$. In the present example, the OCT device 14 is configured such that the scan depth $z_{max}$ is approximately equal to or more than 40 mm. This allows determining all relevant distances Aa, . . . , Lc in the human eye 12. Moreover, as the OCT device 14 is realized by a MEMS-VCSEL device 66, which has a small and compact design, the weight and the volume of the whole system 10 is reduced. The MEMS-VCSEL device 66 has a sweep rate, for example, around 100 kHz to around 1 MHz. This allows a rapid acquisition the OCT data Ia-c and thus a reduction of the biometric properties determination time.

The beam guiding device 18 comprises a scanning unit 68 with at least one pair of mirrors, e.g., galvanometer mirrors or adaptive mirrors, (not shown) rotatable around two perpendicularly oriented rotation axis. The beam guiding device 18 further comprises a focusing device 70, such as a lens, to focus the measuring light beam 16 deflected by the scanning unit 68 onto or into the eye 12 at a focal position x, y, z. The scanning unit 68 is configured to scan the focal position x, y, z in a two-dimensional manner along spatial directions x and y (compare the coordinate system in FIGS. 1 and 2). The focusing device 70 is configured such that a lateral resolution of the OCT data is less than 100 μm, e.g., 50 μm. The focal length of the focusing device 70 is changeable along spatial direction z to scan the focal position x, y, z in a one-dimensional manner along spatial direction z (compare again the coordinate system in FIGS. 1 and 2).

Unless expressly stated otherwise, identical reference symbols in FIGS. 1 to 3 stand for identical or identically-acting elements. Also, an arbitrary combination of the features and/or modifications elucidated in FIGS. 1 to 3 is conceivable.

The invention claimed is:

1. System for determining biometric properties of an eye or parts of the eye, comprising:
   an OCT device configured to emit a measuring light beam;
   a beam guiding device configured to guide the measuring light beam; and
   a control and analysis device configured to control the beam guiding device to guide the measuring light beam towards the eye for a plurality of scans such that for each scan the measuring light beam enters the cornea in a first lateral region and reaches the retina of the eye in a second lateral region along a corresponding beam path, the second lateral region including the fovea of the retina, the beam paths being different from each other, wherein the first lateral region or the second lateral region is a circular region having a diameter of approximately equal to or less than 1 mm;
   the OCT device is further configured to interferometrically analyze the measuring light beam back-reflected from the eye for each scan to provide corresponding OCT data;
   the control and analysis device is further configured to:
      determine on basis of the OCT data for each scan of the plurality of scans at least one distance, wherein the determined distance is a distance from a surface of the retina to a surface of the cornea or a distance from the surface of the retina to a surface of the lens of the eye.

2. System of claim 1, wherein the control and analysis device is further configured to:
   select on basis of the OCT data from the plurality of scans that scan for which the determined distance is maximum; and
   output the OCT data of the selected scan.

3. System of claim 2, wherein the control and analysis device is further configured to:
   determine on basis of the OCT data of the selected scan a position, wherein the determined position is a position of the intersection point of the cornea, a position of a center of the fovea, or a crater bottom of the fovea; and
   determine a visual axis of the eye by associating the visual axis of the eye with a straight line through the determined position.

4. System of claim 1, wherein the control and analysis device is further configured calculate, according to the OCT data from the scans, parameters of an IOL.

5. System of claim 1, wherein the OCT device comprises:
   a micro electro mechanical system with vertical cavity surface emitting laser (MEMS-VCSEL) device for emitting the measuring light beam.

6. System of claim 5, wherein the MEMS-VCSEL device is configured as a swept source optical coherence tomography device with:
   an axial resolution equal to or less than about 10 μm, and a sweep rate around 100 kHz to around 1 MHz.

7. System of claim 1, wherein the control and analysis device is further configured to:
   calculate, according to the OCT data from the scans, an appropriate position of an IOL within the lens.

8. Method for determining biometric properties of an eye or parts of the eye, comprising:
   emitting a measuring light beam;
   guiding the measuring light beam towards the eye for a plurality of scans, for each scan the measuring light beam entering the cornea in a first lateral region and reaching the retina of the eye in a second lateral region along a corresponding beam path, the second lateral region including the fovea of the retina, the beam paths being different from each other, wherein the first lateral region or the second lateral region is a circular region having a diameter of approximately equal to or less than 1 mm;
   interferometrically analyzing the measuring light beam back-reflected from the eye for each scan to provide corresponding OCT data;
   determining, according to the OCT data for each scan of the plurality of scans, at least one distance, wherein the determined distance is a distance from a surface of the retina to a surface of the cornea or a distance from the surface of the retina to a surface of the lens of the eye.

9. Method of claim 8, further comprising:
   selecting, according to the OCT data, the scan for which the determined distance is maximum; and
   outputting the OCT data of the selected scan.

10. Method of claim 9, further comprising:
    determining, according to the OCT data of the selected scan a position, wherein the determined position is a position of the intersection point of the cornea, a position of a center of the fovea, or a crater bottom of the fovea; and
    determining the visual axis of the eye by associating the visual axis of the eye with a straight line through the determined position.

11. Method of claim 8, further comprising:
  calculating, according to the OCT data from the plurality of scans, at least one parameter of an IOL.

12. Method of claim 8, further comprising:
  calculating, according to the OCT data from the plurality of scans, an appropriate position of an IOL within a lens.

* * * * *